United States Patent [19]

Lesieur et al.

[11] Patent Number: 5,166,353
[45] Date of Patent: * Nov. 24, 1992

[54] BENZOTHIAZOLINONE COMPOUNDS

[75] Inventors: Daniel Lesieur, Gondecourt; Charles Lespagnol, Lambersart; Said Yous, Villeneuve d'Ascq, all of France

[73] Assignee: Adir et Compagnie, Neuilly-sur-Seine, France

[*] Notice: The portion of the term of this patent subsequent to Nov. 10, 2009 has been disclaimed.

[21] Appl. No.: 700,571

[22] Filed: May 15, 1991

Related U.S. Application Data

[63] Continuation of Ser. No. 516,066, Apr. 27, 1990.

[30] Foreign Application Priority Data

Apr. 28, 1989 [FR] France ............... 89 05655

[51] Int. Cl.$^5$ ............... C07D 277/62; C07D 417/12
[52] U.S. Cl. ............... 548/165; 546/270
[58] Field of Search ............... 546/270; 548/165; 514/338, 369

[56] References Cited

U.S. PATENT DOCUMENTS 4,562,190  12/1985  Ueda ............... 548/121
4,621,084  11/1986  Takaya ............... 546/121

FOREIGN PATENT DOCUMENTS 2244506  4/1975  France .
7323380  4/1975  France .
2491066  4/1982  France .
8020861  4/1982  France .
60-130573  7/1985  Japan .
60-130574  7/1985  Japan .

8501289  3/1985  World Int. Prop. O. .

OTHER PUBLICATIONS

Eur J Med Chem (1990)25, pp. 361-368, "Amino Ketone and Amino Alcohol Derivatives of Bensoxazolinone: Synthesis, Adrenergic and Antihypertensive Properties", J. P. Bonte, et al.

*Primary Examiner*—C. Warren Ivy
*Assistant Examiner*—Celia Chang
*Attorney, Agent, or Firm*—Gordon W. Hueschen

[57] ABSTRACT

Compounds of general formula(I):

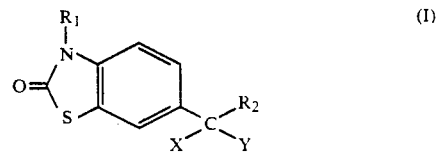

in which:

$R_1$ represents a hydrogen atom or a lower alkyl group, $R_2$ represents a substituted or unsubstitutes alkyl group, a substituted or unsubstituted aryl group, a substituted or unsubstituted alkenyl group, a substituted or unsubstituted thienyl, furyl, pyrrolyl or pyridinyl group, X represents a hydrogen atom, Y represents a hydroxyl group, or else X and Y together represent an oxygen atom, their enantiomers, diastereoisomers and epimers. Medicaments.

5 Claims, No Drawings

BENZOTHIAZOLINONE COMPOUNDS

This is a continuation of application Ser. No. 07/516,066, filed Apr.27, 1990.

The present invention concerns new compounds of benzothiazolinone, their preparation, and pharmaceutical compositions containing them.

Numerous compounds of benzothiazolinone have been described in therapy as possessing very varied pharmacological properties.

The patent JP 86143307 describes in particular 6-alkylbenzothiazolinones as fungicides; the patent JP 85130574 describes 6-amidobenzothiazolinones as cardiac stimulants; and the patent WO 8501289 describes, among others, 6-acylbenzothiazolinones as anti-inflammatory or antithrombic compounds.

As for the patents FR 7323280 and FR 8020861, they describe 6-acylbenzothiazolinones utilizable as analgesics.

The Applicant has now discovered benzothiazolinone compounds having a much greater analgesic activity than that of the compounds . described in the patent FR 7323280.

The compounds of the present invention are in fact completely non-toxic and have intense analgesic properties, and moreover possess a good level of platelet anti-aggregation activity.

Finally, in a surprising manner, they likewise have properties of normalizing blood lipid levels which are of great interest in reducing cholesterolemia by lowering low density atherogenic fractions (VLDL and LDL) and in improving the distribution of plasma cholesterol by increasing the ratio of HDL cholesterol to total cholesterol.

More specifically, the invention concerns compounds of the general formula (I):

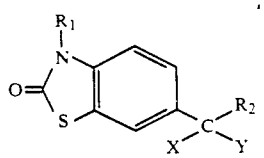
(I)

in which:
$R_1$ represents a hydrogen atom or a lower alkyl group,
$R_2$ represents:
  a straight- or branched-chain lower alkyl group, which may be substituted by one or more halogen atoms or by one or more alkoxy, hydroxy, aryl, or carboxylic acid groups,
  an aryl group which may be substituted by one or more:
    halogen atoms, or
    lower alkyl groups, which may be substituted by one or more halogen atoms, or
    hydroxy or lower alkoxy groups,
  a straight- or branched-chain lower alkenyl group, which may be substituted by a carboxylic acid, alkoxy, hydroxyl or aryl group,
  a 2-thienyl group, which may be substituted by a straight- or branched-chain lower alkyl group,
  a 2-furyl group, which may be substituted by a straight- or branched-chain lower alkyl group,
  a 2-pyrrolyl group, which may be substituted by a straight- or branched-chain lower alkyl group,
  a Pyridyl group, which may be substituted by a straight- or branched-chain lower alkyl group,
X represents a hydrogen atom,
Y represents a hydroxyl group,
or else X and Y together represent an oxygen atom,
the term "lower" indicating that the groups thus qualified have 1-6 carbon, atoms
their enantiomers, diastereoisomers and epimers, as well as, when $R_1$ represents a hydrogen atom and $R_2$ comprises a carboxylic acid group, their addition salts with a pharmaceutically acceptable base, or when $R_2$ comprises an amine-containing group, their addition salts with a pharmaceutically acceptable acid.

Among the bases which can be added to the compounds of formula (I) for which $R_1$ represents a hydrogen atom or when $R_2$ comprises a carboxylic acid group, there can be mentioned, as examples, the hydroxides of sodium, potassium and calcium, or organic bases such as diethylamine, diethanolamine, triethylamine, benzylamine, dicyclohexylamine, arginine, or carbonates of alkali metals or alkaline earth metals.

Among the acids which can be added to the compounds of formula (I) for which $R_2$ comprises an amine-containing group, there can be mentioned as examples hydrochloric, sulfuric, phosphoric, tartaric, malic, maleic, fumaric, oxalic, methanesulfonic, camphoric, citric acids, and the like.

The invention also extends to the process for obtaining compounds of general formula (I), wherein there is utilized as starting material a compounds of formula (II):

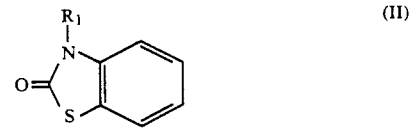
(II)

in which $R_1$ has the same meaning as in formula (I), obtained, for example, by the reaction of ortho-aminothiophenol with urea, followed, when $R_1$ is different from H, by an alkylation on the nitrogen,
which is subjected, depending on the nature of $R_2$:
* either to the action of an acid chloride of formula (III):

in which $R_2$ has the same meaning as in formula (I),
or else of the corresponding acid anhydride or lactone, under conventional conditions of the Friedel-Crafts reaction, preferably using aluminum chloride in the presence of dimethylformamide according to the conditions of THYES et al. (J. Med. Chem., 1983, 26, 6, 800–807),
to obtain a compound of formula (I/a):

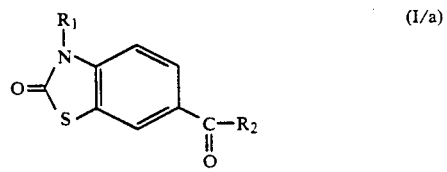
(I/a)

a particular case of the compounds of formula (I), in which:
$R_1$ and $R_2$ have the same meaning as in formula (I), X and Y together represent an oxygen atom,
* or else to the action of an acid of formula (V):

$$R_2-CO_2H \quad (V)$$

in which $R_2$ has the same meaning as in formula (I), or of the corresponding acid chloride or acid anhydride or lactone in the presence of polyphosphoric acid under the conditions described in Patent FR 73/23280, to obtain a compounds of formula (I/a):

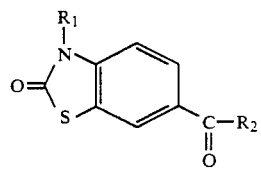

(I/a)

a particular case of the compounds of formula (I), in which:

$R_1$ and $R_2$ have the same meaning as in formula (I),

X and Y together represent an oxygen atom, which compound of Formula (I/a) may be optionally purified by a conventional purification method, and, in the cases where $R_1$ represents a hydrogen atom, or in the cases where $R_2$ comprises a carboxylic acid group or an amine group, may be salified, if desired, with a pharmaceutically acceptable base or acid, respectively, and which, when $R_2$ represents an aryl group substituted by one or more lower alkoxy groups, can be subjected, if desired, to the action of a strong acid, to lead to a compound of formula (I/z):

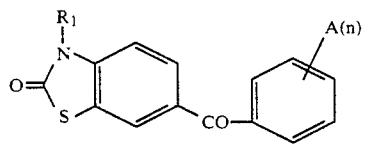

(I/z)

in which $R_1$ has the same meaning as in formula (I), A represents a hydroxy group, and n is an integer comprised between 1 and 5, the position of the hydroxy group(s) being identical to that of the lower alkoxy group(s) of the product of formula (I) subjected to the action of the acid, which product of formula (I/z) may be optionally purified by a conventional method and, in the case where $R_1$ represents a hydrogen atom, may be salified, if desired, with a pharmaceutically acceptable base, which compound of formula (I/a) or (I/z) can, if desired, be subjected to the action of a hydrogenating agent preferably chosen from among a mixed hydride of an alkali metal such as for example sodium borohydride, preferably in the presence of a lower aliphatic alcohol or in acid medium, to lead, after neutralization of the reaction medium if necessary, to a derivative of formula (I/b):

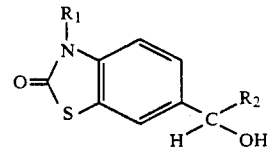

(I/b)

a particular case of the compounds of formula (I) in which:

$R_1$ and $R_2$ have the same meaning as in formula (I),

X represents a hydrogen atom,

Y represents a hydroxyl group, the isomers of which can be separated, if desired, by a conventional separation method, and may be optionally purified by a conventional purification method, and which, in the cases where $R_1$ represents a hydrogen atom, or in the cases where $R_2$ comprises a carboxylic acid group or an amine group, may be salified if desired, with a pharmaceutically acceptable base or acid respectively.

The compounds of formula (I) possess properties of pharmacological interest. The pharmacological study of the compounds of the invention has in fact shown that they had little toxicity, and possessed an analgesic activity and properties of normalization of blood lipids. This spectrum of activity makes the compounds of the present invention advantageous in a certain number of conditions such as rheumatic, neuralgic, or lumbosciatic pains, cervicobrachial neuralgias, traumatic pains such as sprains, fractures, dislocations, post-traumatic pains, postoperative pains, dental pains, neurological pains such as facial neuralgias, visceral pains such as nephritic colics, dysmenorrheas, proctological surgery, pains in the ear, nose and throat region, pancreatites, various pains, headaches, cancer pains, pains in the case of isolated or associated endogenous hypercholesterolemias and hypertriglyceremias, as well as the prevention of peripheral and cerebrovascular arterial ischemic diseases.

The present invention likewise has as subject the pharmaceutical compositions containing the products of formula (I), alone or in combination with one or more inert, nontoxic, pharmaceutically acceptable excipients or vehicles.

Among the pharmaceutical compositions according to the invention, there can be cited more particularly those which are suitable for oral, parenteral, or nasal administration, simple or coated tablets, sublingual tablets, sachets, packets, gelatin capsules, sublinqual preparations, lozenges, suppositories, creams, ointments, skin gels, and the like.

The appropriate dosage varies according to the age and weight of the patient, the administration route, the nature of the therapeutic indication, or any associated treatments, and is graded between 1 centigram and 4 grams per 24 hours.

The following examples illustrate the invention and do not limit it in any way.

EXAMPLE 1:
6-BENZOYLBENZOTHIAZOLINONE

To a solution of 0.04 mol of benzothiazolinone in 150 g of polyphosphoric acid there is slowly added, with agitation, 0.05 mol of benzoic acid. The reaction medium is heated to 130° C. for 4 hours. After cooling, the mixture is hydrolyzed in 10 volumes of ice-cold water.

The precipitate obtained is drained, washed with water until the filtrate is neutral, and dried.

The product is recrystallized from ethanol.

Yield: 80%

Melting point: 216-217° C.

Infrared: $\nu$ CO (thiocarbamate): 1680 cm$^{-1}$ $\nu$ CO (ketone): 1630 cm$^{-1}$

| Elementary microanalysis: | | | | |
|---|---|---|---|---|
| | C % | H % | N % | S % |
| Calculated | 65.86 | 3.55 | 5.49 | 12.56 |
| Found | 65.69 | 3.60 | 5.39 | 12.63 |

EXAMPLE 2:
3-METHYL-6-BENZOYLBENZOTHIAZOLINONE

The procedure is the same as in Example 1, but replacing the benzothiazolinone by 3-methylbenzothiazolinone and maintaining agitation for 5 hours at 120° C.

The product is recrystallized from absolute ethanol.
Yield: 82%
Melting point: 148° C.
Infrared: $\nu$ CO (thiocarbamate): 1685 cm$^{-1}$
$\nu$ CO (ketone): 1635 cm$^{-1}$

| Elementary microanalysis: | | | |
|---|---|---|---|
| | C % | H % | N % |
| Calculated | 66.89 | 4.12 | 5.20 |
| Found | 66.69 | 4.14 | 5.22 |

EXAMPLE 3:
6-(4-CHLOROBENZOYL)BENZOTHIAZOLINONE

The procedure is the same as in Example 1, but replacing the benzoic acid by 4-chlorobenzoic acid, and maintaining the agitation for 1 hour 30 minutes at 145° C.

The product is recrystallized from absolute ethanol
Yield: 75%
Melting point: >270° C.
Infrared: $\nu$ CO (thiocarbamate): 1730 cm$^{-1}$
$\nu$ CO (ketone): 1630$^{-1}$

| Elementary microanalysis: | | | | |
|---|---|---|---|---|
| | C % | H % | N % | CL % |
| Calculated | 58.03 | 2.78 | 4.83 | 12.37 |
| Found | 57.84 | 2.81 | 4.99 | 12.22 |

EXAMPLE 4:
3-METHYL-6-(4-CHLOROBENZOYL)BENZOTHIAZOLINONE

The procedure is the same as in Example 3, but replacing the benzothiazolinone by 3-methylbenzothiazolinone and maintaining agitation for 2 hours at 140° C.

The product is recrystallized from ethanol.
Yield: 78%
Melting point: 169-170° C.
Infrared $\nu$ CO (thiocarbamate): 1700 cm$^{-1}$
$\nu$CO(ketone): 1635 cm$^{-1}$

| Elementary microanalysis: | | | | | |
|---|---|---|---|---|---|
| | C % | H % | N % | Cl % | S % |
| Calculated | 59.31 | 3.32 | 4.61 | 11.67 | 10.55 |
| Found | 59.15 | 3.15 | 4.57 | 11.55 | 10.66 |

EXAMPLE 5:
6-PROPIONYLBENZOTHIAZOLINONE

The procedure is the same as in Example 1, but replacing the benzoic acid by propionic acid, and maintaining the agitation for 4 hours at 100° C.

The product is recrystallized from propanol.
Yield: 30%
Melting point: 204-205° C.
Infrared $\nu$ CO (thiocarbamate): 1690 cm$^{-1}$
$\nu$ CO (ketone): 1650 cm$^{-1}$

| Elementary microanalysis: | | | | |
|---|---|---|---|---|
| | C % | H % | N % | S % |
| Calculated | 57.95 | 4.39 | 6.76 | 15.47 |
| Found | 57.88 | 4.26 | 6.65 | 15.03 |

EXAMPLE 6:
6-(3-METHYLPROPIONYL)BENZOTHIAZOLINONE

The procedure is the same as in Example 5, but replacing with the benzothiazolinone by 3-methylbenzothiazolinone, and maintaining the agitation for 2 hours 30 minutes at 90° C.

The product is recrystallized from ethanol.
Yield: 60%
Melting point: 178° C.
Infrared: $\nu$ CO: 1655 cm$^{-1}$ (thiocarbamate and ketone)

| Elementary microanalysis: | | | |
|---|---|---|---|
| | C % | H % | N % |
| Calculated | 59.71 | 5.01 | 6.33 |
| Found | 59.44 | 5.06 | 6.31 |

EXAMPLE 7:
6-BUTYRYLBENZOTHIAZOLINONE

The procedure is the same as in Example 1, but replacing the benzoic acid by butyric acid, and maintaining the temperature at 90° C. for 4 hours.

The product is recrystallized from ethanol.
Yield: 50%
Melting point: 143-145° C.
Infrared: $\nu$ CO (thiocarbamate): 1685 cm$^{-1}$
$\nu$ CO (ketone): 1660$^{-1}$

| Elementary microanalysis: | | | | |
|---|---|---|---|---|
| | C % | H % | N % | S % |
| Calculated | 59.70 | 4.97 | 6.33 | 14.49 |
| Found | 59.31 | 5.05 | 6.30 | 14.52 |

EXAMPLE 8:
3-METHYL-6-BUTYRYLBENZOTHIAZOLINONE

The procedure is the same as in Example 7, but replacing the benzothiazolinone by 3-methylbenzothiazolinone and maintaining agitation for 3 hours at 100° C.

The product is recrystallized from ethanol.
Yield: 55%
Melting point: 115-116 C.
Infrared: $\nu$ CO (thiocarbamate): 1675 cm$^{-1}$ ν CO (ketone): 1660 cm$^{-1}$

| Elementary microanalysis: | | | |
|---|---|---|---|
| | C % | H % | S % |
| Calculated | 61.25 | 5.57 | 13.63 |
| Found | 61.43 | 5.64 | 13.82 |

EXAMPLE 9:
6-VALERYLBENZOTHIAZOLINONE

The procedure is the same as in Example 1, but replacing the benzoic acid by valeric acid and maintaining agitation for 2 hours 30 minutes at 100° C.

The product is recrystallized from absolute ethanol.
Yield: 57%
Melting point: 142–143° C.
Infrared: ν CO (thiocarbamate): 1690 cm$^{-1}$
ν CO (ketone): 1665 cm$^{-1}$

| Elementary microanalysis: | | | | |
|---|---|---|---|---|
| | C % | H % | N % | S % |
| Calculated | 61.25 | 5.57 | 5.95 | 13.63 |
| Found | 61.21 | 5.58 | 5.95 | 13.74 |

EXAMPLE 10:
3-METHYL-6-VALERYLBENZOTHIAZOLINONE

The procedure is the same as in Example 9, but replacing the benzothiazolinone by 3-methylbenzothiazolinone and maintaining agitation for 3 hours at 100° C.

The product is recrystallized from absolute ethanol.
Yield: 60%
Melting point: 93–94° C.
Infrared: ν CO (thiocarbamate): 1680 cm$^{-1}$
ν CO (ketone): 1660 cm$^{-1}$

| Elementary microanalysis: | | | |
|---|---|---|---|
| | C % | H % | S % |
| Calculated | 62.62 | 6.04 | 12.86 |
| Found | 62.80 | 6.00 | 13.13 |

EXAMPLE 11:
6-(2-THENOYL)BENZOTHIAZOLINONE

The procedure is the same as in Example 1, but replacing the benzoic acid by 2-thiophenecarboxylic acid, and maintaining the agitation for 5 hours at 75° C.

The product is recrystallized from absolute ethanol.
Yield: 20%
Melting point: 224° C.
Infrared: ν CO (thiocarbamate): 1735 cm$^{-1}$
ν CO (ketone): 1620 cm$^{-1}$

| Elementary microanalysis: | | | |
|---|---|---|---|
| | C % | H % | N % |
| Calculated | 55.15 | 2.70 | 5.36 |
| Found | 54.63 | 2.68 | 5.13 |

EXAMPLE 12:
3-METHYL-6-(2-THENOYL)BENZOTHIAZOLINONE

The procedure is the same as in Example 11, but replacing the benzothiazolinone by 3-methylbenzothiazolinone and maintaining agitation for 5 hours at 80° C.

The product is recrystallized from absolute ethanol.
Yield: 36%
Melting point: 164–165° C.
Infrared ν CO (thiocarbamate): 1660 cm$^{-1}$
ν CO (ketone): 1620 cm$^{-1}$

| Elementary microanalysis: | | | |
|---|---|---|---|
| | C % | H % | S % |
| Calculated | 56.70 | 3.29 | 23.29 |
| Found | 56.56 | 3.38 | 23.00 |

EXAMPLE 13:
6-(4-HYDROXYBUTYRYL)BENZOTHIAZOLINONE

The procedure is the same as in Example 1, but replacing the benzoic acid by γ-butyrolactone and maintaining agitation for 2 hours at 165° C.

The product is recrystallized from ethyl acetate.
Yield: 30%
Melting point: 159–161° C.
Infrared: ν CO (thiocarbamate): 1680 cm$^{-1}$
ν CO (ketone): 1660 cm$^{-1}$

| Elementary microanalysis: | | | |
|---|---|---|---|
| | C % | H % | S % |
| Calculated | 55.67 | 4.67 | 13.51 |
| Found | 55.68 | 4.68 | 13.44 |

EXAMPLE 14:
3-METHYL-6-(4-HYDROXYBUTYRYL)BENZOTHIAZOLINONE

The procedure is the same as in Example 13, but replacing the benzothiazolinone by 3-methylbenzothiazolinone.

EXAMPLE 15:
6-ACETYLBENZOTHIAZOLINONE

To a solution containing 0.5 mol of anhydrous aluminium chloride in 0.20 mol of dimethylformamide is added 0.05 mol of benzothiazolinone, then, slowly and with agitation, 0.06 mol of acetyl chloride.

The reaction medium is heated for 3 hours at 80° C.

After cooling, the mixture is hydrolyzed in ice-cold water. The precipitate obtained is drained, washed with water until the filtrate is neutral, and dried.

The product is recrystallized from ethanol
Yield: 60%
Melting point: 189–191° C.
Infrared: ν CO (thiocarbamate): 1700 cm$^{-1}$
ν CO (ketone): 1660 cm$^{-1}$

| Elementary microanalysis: | | |
|---|---|---|
| | C % | H % |
| Calculated | 55.94 | 3.65 |

EXAMPLE 16: 3-METHYL-6-ACETYLBENZOTHIAZOLINONE

The procedure is the same as in Example 15, but replacing the benzothiazolinone by 3-methylbenzothiazolinone and maintaining agitation for 4 hours at 75° C.

The product is recrystallized from absolute ethanol.
Yield: 62%
Infrared: $\nu$ CO (thiocarbamate): 1675 cm$^{-1}$
$\nu$ CO (ketone): 1660 cm$^{-1}$
Calculated 57.95 4.37

| | Elementary microanalysis: | |
|---|---|---|
| | C % | H % |
| Calculated | 57.95 | 4.37 |
| Found | 58.24 | 4.27 |

EXAMPLE 17: 6-BROMOACETYLBENZOTHIAZOLINONE

The procedure is the same as in Example 15, but replacing the acetyl chloride by bromoacetyl chloride and maintaining agitation for one hour at 60° C.
The product is recrystallized from dioxane.
Yield: 65%
Melting point: 240° C.
Infrared: $\nu$ CO (thiocarbamate): 1700 cm$^{-1}$
$\nu$ CO (ketone): 1670 cm$^{-1}$

EXAMPLE 18: 3-METHYL-6-BROMOACETYLBENZOTHIAZOLINONE

The procedure is the same as in Example 17, but replacing the benzothiazolinone by 3-methylbenzothiazolinone and maintaining agitation for one hour at 65° C.
The product is recrystallized from ethanol
Yield: 66%
Melting point: 164–165° C.
Infrared: $\nu$ CO (thiocarbamate): 1675 cm$^{-1}$
$\nu$ CO (ketone): 1655 cm$^{-1}$

EXAMPLE 19: 6-(3-CHLOROPROPIONYL)BENZOTHIAZOLINONE

The procedure is the same as in Example 15, but replacing the acetyl chloride by 3-chloropropionyl chloride and maintaining agitation for 2 hours at 80° C.
The product is recrystallized from absolute ethanol.
Yield: 55%
Melting point: 174–175° C.
Infrared: $\nu$ CO (thiocarbamate and ketone): between 1680 cm$^{-1}$ and 1650 cm$^{-1}$

| | Elementary microanalysis: | |
|---|---|---|
| | C % | H % |
| Calculated | 49.69 | 3.33 |
| Found | 49.51 | 3.42 |

| | Elementary microanalysis: | |
|---|---|---|
| | C % | H % |
| Found | 56.03 | 3.61 |

EXAMPLE 20: 3-METHYL-6-(3-CHLOROPROPIONYL)BENZOTHIAZOLINONE

The procedure is the same as in Example 19, but replacing the benzothiazolinone by 3-methylbenzothiazolinone and maintaining agitation for 2 hours at 85° C.

The product is recrystallized from ethanol.
Yield: 54%
Melting point: 128–129° C.
Infrared: $\nu$ CO (thiocarbamate and ketone): 1660 cm$^{-1}$

| | Elementary microanalysis: | |
|---|---|---|
| | C % | H % |
| Calculated | 51.66 | 3.94 |
| Found | 51.67 | 3.83 |

EXAMPLE 21: 6-(3-CARBOXYPROPIONYL)BENZOTHIAZOLINONE

The procedure is the same as in Example 15, but replacing the acetyl chloride by succinic anhydride and maintaining agitation for 4 hours at 70° C.
The product is recrystallized from ethanol.
Yield: 55%
Melting point: 242° C.
Infrared: $\nu$ CO (thiocarbamate) : 1680 cm$^{-1}$
$\nu$ CO (ketone) : 1650 cm$^{-1}$

| | Elementary microanalysis: | | |
|---|---|---|---|
| | C % | H % | S % |
| Calculated | 52.58 | 3.61 | 12.76 |
| Found | 52.51 | 3.54 | 13.10 |

EXAMPLE 22: 3-METHYL-6-(3-CARBOXYPROPIONYL)BENZOTHIAZOLINONE

The procedure is the same as in Example 21, but replacing the benzothiazolinone by 3-methylbenzothiazolinone and maintaining agitation for 3 hours at 75° C.

The product is recrystallized from ethanol.
Yield: 60%
Melting point: 226–227° C.
Infrared: $\nu$ CO (thiocarbamate): 1670 cm$^{-1}$
$\nu$ CO (ketone): 1650 cm$^{-1}$

| | Elementary microanalysis: | |
|---|---|---|
| | C % | H % |
| Calculated | 54.32 | 4.18 |
| Found | 54.50 | 4.21 |

EXAMPLE 23: 6-(3-CARBOXY-1-OXO-3-BUTENYL)BENZOTHIAZOLINONE

The procedure is the same as in Example 15, but replacing the acetyl chloride by itaconic anhydride and maintaining agitation for 6 hours at 75° C.
The product is recrystallized from ethyl acetate.
Yield: 30% 5 Melting point: 227–230° C.

Infrared: ν CO (thiocarbamate): 1670 cm$^{-1}$
ν CO (ketone) : 1635 cm$^{-1}$

| Elementary microanalysis: | | | |
|---|---|---|---|
| | C % | H % | S % |
| Calculated | 54.74 | 3.44 | 12.16 |
| Found | 54.81 | 3.42 | 12.17 |

EXAMPLE 24:
3-METHYL-6-(3-CARBOXY-1-OXO-3-BUTENYL)-BENZOTHIAZOLINONE

The procedure is the same as in Example 23, but replacing the benzothiazolinone by 3-methylbenzothiazolinone.

EXAMPLE 25:
6-NICOTINOYLBENZOTHIAZOLINONE

The procedure is the same as in Example 15, but replacing the acetyl chloride by nicotinyl chloride hydrochloride and maintaining agitation for 30 hours at 100° C.
The product is recrystallized from ethanol.
Yield: 73%
Melting point: 237-239° C.
Infrared: ν CO (thiocarbamate): 1720 cm$^{-1}$
ν CO (ketone): 1635 cm$^{-1}$

| Elementary microanalysis: | | | |
|---|---|---|---|
| | C % | H % | S % |
| Calculated | 60.92 | 3.14 | 12.51 |
| Found | 61.12 | 3.13 | 12.36 |

EXAMPLE 26:
3-METHYL-6-NICOTINOYLBENZOTHIAZOLINONE

The procedure is the same as in Example 25, but replacing the benzothiazolinone by 3-methylbenzothiazolinone and maintaining agitation for 30 hours at 90° C.
The product is recrystallized from ethanol
Yield: 76%
Melting point: 176-178° C.
Infrared: ν CO (thiocarbamate): 1670 cm$^-$
ν CO (ketone): 1640 cm$^{-1}$

| Elementary microanalysis: | | | |
|---|---|---|---|
| | C % | H % | S % |
| Calculated | 62.20 | 3.73 | 11.86 |
| Found | 62.19 | 3.67 | 11.55 |

EXAMPLE 27:
3-METHYL-6-(1-HYDROXY-1-PHENYLMETHYL)BENZOTHIAZOLINONE 0.02 mol of 3-methyl-6-benzoylbenzothiazolinone prepared in Example 2 are dissolved, with magnetic stirring, in 200 cm$^3$ of methanol in a 250 cm$^3$ flask 0.04 mol of sodium borohydride is added very slowly, with agitation. The agitation is maintained for 4 hours at ambient temperature. The reaction medium is evaporated under vacuum on a water bath. The residue is taken up in water, and the precipitate formed is drained and dried.

The product is recrystallized from toluene.
Yield: 92%
Melting point: 129-130° C.
Infrared: ν CO (thiocarbamate): 1635 cm$^{-1}$

EXAMPLE 28: 6-(1-HYDROXY-1-PHENYLMETHYL)BENZOTHIAZOLINONE 0.02 mol of 6-benzoylbenzothiazolinone obtained in Example 1 are dissolved in 80 cm$^3$ of 30% aqueous sodium carbonate solution in a 250 cm$^3$ flask 0.015 mol of sodium borohydride are added slowly, with agitation. The agitation is maintained for 16 hours at ambient temperature, followed by acidification with hydrochloric acid diluted 1:1. The precipitate formed is drained, washed with water and dried.
The product is recrystallized from acetonitrile
Yield: 91%
Melting point: 159-160° C.
Infrared ν CO (thiocarbamate) : 1645 cm$^{-1}$

EXAMPLE 29:
6-(2,6-DICHLOROBENZOYL)BENZOTHIAZOLINONE

The procedure is as in Example 1, but replacing the benzoic acid by 2,6-dichlorobenzoic acid.
Recrystallization solvent methanol.
Melting point: >260° C.

EXAMPLE 30:
6-(p-ANISOYL)BENZOTHIAZOLINONE or 6-(4METHOXYBENZOYL)BENZOTHIAZOLINONE

The procedure is as in Example 1, but replacing the benzoic acid by p-anisic acid, and maintaining agitation for 4 hours at 120-123° C.
Recrystallization solvent dioxane
Melting point: 226-228° C.

EXAMPLE 31:
6-BENZOYLBENZOTHIAZOLINONE, DIETHANOLAMINE SALT 0.04 mol of 6-benzoylbenzothiazolinone is dissolved in 150 cm$^3$ of dioxane in a 250 cm$^3$ flask. 0.04 mol of diethanolamine is added dropwise, with magnetic stirring. Agitation is continued for two hours. The product is drained, dried, and recrystallized from dioxane.
Melting point: 175° C.

EXAMPLE 32:
6-BENZOYLBENZOTHIAZOLINONE, SODIUM SALT 0 04 gram-atom of sodium is added to a 250 cm$^3$ round-bottom flask containing 60 cm$^3$ of ethanol and left to stand. 0.04 mol of 6-benzoylbenzothiazolinone is added, with magnetic stirring Agitation is continued for one hour. The mixture is taken to dryness. The residue is heated to boiling in 80 cm$^3$ of dioxane, and drained hot.
Melting point: >260° C.

EXAMPLE 33:
6-PHENYLACETYLBENZOTHIAZOLINONE

This product is obtained by proceeding as in Example 1, but replacing the benzoic acid by phenylacetic acid.

EXAMPLE 34: 6-(p-TOLUYL)BENZOTHIAZOLINONE

This product is obtained by proceeding as in Example 1, but replacing the benzoic acid by para-toluic acid.

EXAMPLE 35:6-(4-TRIFLUOROMETHYLBENZOYL)BENZOTHIAZOLINONE

This product is obtained by proceeding as in Example 1, but replacing the benzoic acid by 4-trifluoromethylbenzoic acid.

EXAMPLE 36: 6-(3,4,5-TRIMETHOXYBENZOYL)BENZOTHIAZOLINONE

The procedure is as in Example 1, but replacing the benzoic acid by 3,4,5-trimethoxybenzoic acid.

EXAMPLE 37: 6-(4-HYDROXYBENZOYL)BENZOTHIAZOLINONE 0.02 mol of 6-(4-methoxybenzoyl)benzothiazolinone obtained in Example 30 are placed in a mixture of 15 cc of 47% hydrobromic acid and 15 cc of acetic acid. The mixture is refluxed with agitation for 72 hours. It is allowed to cool and the product is drained, dried, washed with water, and recrystallized from alcohol at 95° C.

Melting point: >265° C.

EXAMPLE 38: 6-[1-HYDROXY-1-(4-METHOXYPHENYL) METHYL]BENZOTHIAZOLINONE

The procedure is as in Example 28, but replacing the 6benzoyl benzothiazolinone by 6-(4-methoxybenzoyl) benzothiazolinone obtained in Example 30. The agitation is maintained for 5 days.

The product is recrystallized from ethanol diluted 1:1.

Melting point: 169-170° C.

EXAMPLE 39: 6-[1-HYDROXY-1-(4-CHLOROPHENYL) METHYL]BENZOTHLAZOLINONE

The procedure is as in Example 38, but replacing the 6-(4-emethoxybenzoyl-1)benzothiazolinone by 6-(4-chloro-obtained in Example 3.

Melting point: 154-155° C.

EXAMPLE 40: 6-[1-HYDROXYPENTYL]BENZOTHIAZOLINONE

The procedure is as in Example 28, but replacing the 6-benzoyl benzothiazolinone by the 6-valerylbenzothiazolinone obtained in Example 9. The agitation is maintained for 48 hours.

The product is recrystallized from toluene.

Melting point: 125-126° C.

PHARMACOLOGICAL STUDY OF THE DERIVATIVES OF THE INVENTION

EXAMPLE 41: STUDY OF ACUTE TOXICITY

Acute toxicity was assessed after oral administration to groups of 8 mice (26±2 grams) of a dose of 650 mg/kg. The animals were observed at regular intervals during the first day and daily during the 2 weeks following the treatment.

It appeared that the compounds of the invention are totally non-toxic. No death was observed after administration of a dose of 650 mg/kg. No adverse signs were observed after administration of this dose.

EXAMPLE 42: STUDY OF ANALGESIC ACTIVITY

The activity against pain was researched in mice (23-25 g), according to a protocol derived from the method described by SIEGMUND (E.A. SIEGMUND, R.A. CADMUS & GOLU, J. Pharm. Exp. Ther. 119, 1874, 1954). The mice, divided by randomization into lots of 12 animals, received the oral treatment (excipient for the controls) 1 hour before the intraperitoneal injection of a 0.02% aqueous alcoholic solution of p-phenylbenzoquinone (Sigma). The stretching movements were counted between the 5th and 10th minute after the injection.

The percentage activity obtained was evaluated for each dose (% of diminution of the number of stretchings movements for the treated animals with respect to the controls). An ED.:, dose resulting in an activity of 50%, was determined for each product.

It was apparent that certain compounds of the invention possessed a very advantageous analgesic activity. Thus, the $ED_{50}$ of the compound of Example 1 is in the neighborhood of 2 mg/kg.

By way of comparison, the administration of a dose of 100 mg/kg of the derivatives of French Patent 73.23280 gave rise to a percentage of analgesia, in a comparable test, of the order of 25 to 60%, and the compound of French Patent 80.20861, the analgesic activity of which is the most advantageous, had an $ED_{50}$ of 9 mg/kg in this same test of Siegmund, i.e., about 4 times greater than that of the most advantageous product of the present invention.

EXAMPLE 43: STUDY OF BLOOD LIPID-NORMALIZING ACTIVITY

The blood lipid-normalizing activity was studied in mice (26-29 g) according to a protocol described by J.C. Fruchart et al. (Artheroslerosis, 70 (1988), 107-114), enabling the total cholesterol level to be measured as well as the level of HDL cholesterol in animals which had received a standard or a hypercholesterolemic diet.

It was apparent that the compounds of the invention possess an activity in normalizing blood lipids which is of great interest. Thus the compound described in Example 1 shows a diminution of the level of total cholesterol of about 30% while increasing the level of HDL cholesterol by about 30%, which is comparable to the blood lipid-normalizing activity displayed by fenofibrate used as a reference control.

EXAMPLE 44: STUDY OF THE PLATELET ANTI-AGGREGATION ACTIVITY

A plasma rich in platelets was prepared from citrated human blood from donors who had taken no medicament during the ten days before phlebotomy.

Platelet aggregation in this plasma medium was studied by turbidimetry, using appropriate concentrations of an agonist such as ADP, adrenaline, collagen, or arachidonic acid. The products of the invention were added to the plasma three minutes before the agonist.

The products of the invention show a significant antagonist activity against platelet aggregation.

EXAMPLE 45: PHARMACEUTICAL COMPOSITION: TABLETS

Tablets containing a dose of 100 mg of 6-benzoylbenzo-thiazolinone

| Preparation formula for 1000 tablets: | |
|---|---|
| 6-benzoylbenzothiazolinone | 100 g |
| Wheat starch | 15 g |
| Maize starch | 15 g |
| Lactose | 65 g |
| Magnesium stearate | 2 g |
| Silica | 1 g |
| Hydroxypropylcellulose | 2 g |

I claim:

1. A compound selected from those of formula (I):

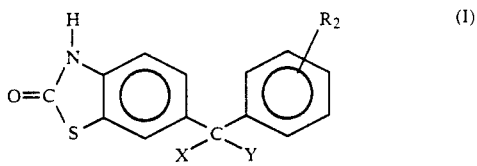

where $R_2$ represents hydrogen, halogen, or hydroxy,
X represents hydrogen,
Y represents a hydroxy group, or alternatively
X and Y together represent an oxygen atom, an anantiomer, a diastereoisomer, and apimer thereof, as well as an addition salt thereof with a pharmaceutically-acceptable base.

2. A compound of claim 1 wherein the compound is 6-benzoyl-benzothiazolinone.

3. A compound of claim 1 wherein the compound is 6-(1-hydroxy-1-phenylmethyl)benzothiazolinone.

4. A compound of claim 1 wherein the compound is 6-(4-hydroxy-benzoyl)benzothiazolinone.

5. A compound of claim 1 wherein the compound is 6-[1-hydroxy-1-(4-chlorophenyl)methyl]benzothiazolinone.

* * * * *

UNITED STATES PATENT AND TRADEMARK OFFICE
CERTIFICATE OF CORRECTION

PATENT NO. : 5,166,353  Page 1 of 2

DATED : Nov. 24, 1992

INVENTOR(S) : Daniel Lesieur, Charles Lespagnol, Said Yous

It is certified that error appears in the above-identified patent and that said Letters Patent is hereby corrected as shown below: item [57]

Title Page, ABSTRACT, 4th line after the formula; "unsubstitutes" should read -- unsubstituted --.

Column 1, line 5; "1990." should read -- 1990, U. S. Patent No. 5,162,350. --

Column 2, line 1; "Pyridyl" should read -- pyridyl --.

Column 6, line 30; "$cm^{31}$ $^1$" should read -- $cm^{-1}$ --.

Column 9, approximately lines 15/16;
 "Yield 62%     should read -- Yield:  62%
   Infrared:"                    Melting point:  145-146° C
                                 Infrared: --

Column 9, line 17; "$cm^{31}$ $^1$" should read -- $cm^{-1}$ --.

Column 9, line 18; delete the line "Calculated 57.95 4.37"

Column 9, approximately line 36; "$cm^{31}$ $^1$" should read --$cm^{-1}$ --.

Column 9, approximately line 50; "$cm^{31}$ $^1$" should read --$cm^{-1}$ --

Column 10, approximately line 23; "21:6-"; move the "21:" to the previous line and insert after "EXAMPLE"

Column 10, line 31; "$cm^{31}$ $^1$" should read -- $cm^{-1}$ --.

Column 12, approximately line 32; "6-(4METHOXYBENZOYL)" should read -- 6-(4-METHOXYBENZOYL) --.

Column 12, approximately line 37; "20 for" should read -- for --.

Column 12, line 56; "0 04" should read -- 0.04 --.

Column 13, line 37; "6benzoyl" should read -- 6-benzoyl --.

Column 13, approximately line 45; "BENZOTHLAZOLINONE" should read -- BENZOTHIAZOLINONE --.

UNITED STATES PATENT AND TRADEMARK OFFICE
CERTIFICATE OF CORRECTION

PATENT NO. : 5,166,353

DATED : Nov. 24, 1992

INVENTOR(S) : Daniel Lesieur, Charles Lespagnol, Said Yous

It is certified that error appears in the above-identified patent and that said Letters Patent is hereby corrected as shown below:

Column 13, approximately line 48; "-emethoxybenzoyl-" should read -- methoxybenzoyl- --.
Column 13, approximately line 50; "chloro-obtained" should read -- chloro-benzoyl) benzothiazolinone obtained --.
Column 14, approximately line 24; "An ED.:," should read -- An $ED_{50}$, --.
Column 16, line 13; "and apimer" should read -- and an epimer --.
                        last line)

Signed and Sealed this

Eleventh Day of January, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,166,353

DATED : Nov. 24, 1992

Page 1 of 2

INVENTOR(S) : Daniel Lesieur, Charles Lespagnol, Said Yous

It is certified that error appears in the above-identified patent and that said Letters Patent is hereby corrected as shown below:

Title Page, ABSTRACT, 4th line after the formula; "unsubstitutes" should read -- unsubstituted --.

Column 1, line 5; "1990." should read -- 1990, U. S. Patent No. 5,162,350. --

Column 2, line 1; "Pyridyl" should read -- pyridyl --.

Column 6, line 30; "cm$^{31\ 1}$" should read -- cm$^{-1}$ --.

Column 9, approximately lines 15/16;
"Yield 62%    should read -- Yield: 62%
  Infrared:"                    Melting point:  145-146° C
                                Infrared: --

Column 9, line 17; "cm$^{31\ 1}$" should read -- cm$^{-1}$ --.

Column 9, line 18; delete the line "Calculated 57.95 4.37"

Column 9, approximately line 36; "cm$^{31\ 1}$" should read --cm$^{-1}$ --.

Column 9, approximately line 50; "cm$^{31\ 1}$" should read --cm$^{-1}$ --

Column 10, approximately line 23; "21:6-"; move the "21:" to the previous line and insert after "EXAMPLE"

Column 10, line 31; "cm$^{31\ 1}$" should read -- cm$^{-1}$ --.

Column 12, approximately line 32; "6-(4METHOXYBENZOYL)" should read -- 6-(4-METHOXYBENZOYL) --.

Column 12, approximately line 37; "20 for" should read -- for --.

Column 12, line 56; "0 04" should read -- 0.04 --.

Column 13, line 37; "6benzoyl" should read -- 6-benzoyl --.

Column 13, approximately line 45; "BENZOTHLAZOLINONE" should read -- BENZOTHIAZOLINONE --.

UNITED STATES PATENT AND TRADEMARK OFFICE
CERTIFICATE OF CORRECTION

PATENT NO. : 5,166,353

DATED : Nov. 24, 1992

INVENTOR(S) : Daniel Lesieur, Charles Lespagnol, Said Yous

It is certified that error appears in the above-identified patent and that said Letters Patent is hereby corrected as shown below:

Column 13, approximately line 48; "-emethoxybenzoyl-" should read -- methoxybenzoyl- --.
Column 13, approximately line 50; "chloro-obtained" should read -- chloro-benzoyl) benzothiazolinone obtained --.
Column 14, approximately line 24; "An ED.:," should read -- An $ED_{50}$, --.
Column 16, line 13; "and apimer" should read -- and an epimer --.

This certificate supersedes Certificate of Correction issued January 11, 1994.

Signed and Sealed this

Thirteenth Day of September, 1994

Attest:

BRUCE LEHMAN

Attesting Officer

Commissioner of Patents and Trademarks